United States Patent
Nakata et al.

(10) Patent No.: US 9,675,320 B2
(45) Date of Patent: Jun. 13, 2017

(54) DIAGNOSTIC ULTRASOUND APPARATUS

(71) Applicants: Masahiko Nakata, Okayama (JP); HITACHI ALOKA MEDICAL, LTD., Mitaka-shi, Tokyo (JP)

(72) Inventors: Masahiko Nakata, Okayama (JP); Eiji Kasahara, Mitaka (JP); Masaru Murashita, Mitaka (JP)

(73) Assignee: Hitachi, Ltd., Tokyo (JP)

( * ) Notice: Subject to any disclaimer, the term of this patent is extended or adjusted under 35 U.S.C. 154(b) by 313 days.

(21) Appl. No.: 14/373,851

(22) PCT Filed: Feb. 26, 2013

(86) PCT No.: PCT/JP2013/054965
§ 371 (c)(1),
(2) Date: Jul. 22, 2014

(87) PCT Pub. No.: WO2013/146016
PCT Pub. Date: Oct. 3, 2013

(65) Prior Publication Data
US 2015/0032001 A1 Jan. 29, 2015

(30) Foreign Application Priority Data
Mar. 26, 2012 (JP) .................... 2012-069055

(51) Int. Cl.
A61B 8/08 (2006.01)
A61B 8/02 (2006.01)
(Continued)

(52) U.S. Cl.
CPC ............ A61B 8/0866 (2013.01); A61B 8/02 (2013.01); A61B 8/0883 (2013.01); A61B 8/463 (2013.01);
(Continued)

(58) Field of Classification Search
None
See application file for complete search history.

(56) References Cited

U.S. PATENT DOCUMENTS

2004/0015081 A1  1/2004  Kramer et al.
2004/0186387 A1  9/2004  Kosuda et al.
(Continued)

FOREIGN PATENT DOCUMENTS

CN    1550206 A    12/2004
CN  102188263 A     9/2011
(Continued)

OTHER PUBLICATIONS

English translation of JP 2010-233966 provided by IPDL.*
(Continued)

Primary Examiner — Katherine Fernandez
(74) Attorney, Agent, or Firm — Westerman, Hattori, Daniels & Adrian, LLP

(57) ABSTRACT

In tomographic image data, a reference region-setting unit (30) sets a body reference region for the body of a fetus and sets a cardiac reference region for the heart of the fetus. A body shift analysis unit (50) analyzes the movement of the fetus' body in the tomographic image data using the body reference region and obtains body shift information. A cardiac motion analysis unit (60) analyzes the movement of the fetus' heart in the tomographic image data using the cardiac reference region and obtains cardiac motion information. Once body shift information and cardiac motion information are obtained in this manner, a pulse information-processing unit (70) obtains fetal pulse information on the basis of the cardiac motion information from which the body shift information has been subtracted. The pulse information obtained by the pulse information-processing unit (70) is displayed on the display unit (80).

12 Claims, 6 Drawing Sheets

(51) Int. Cl.
*A61B 8/00* (2006.01)
*G06T 7/246* (2017.01)
*A61B 8/14* (2006.01)

(52) U.S. Cl.
CPC ............ *A61B 8/469* (2013.01); *A61B 8/5223* (2013.01); *G06T 7/248* (2017.01); *A61B 8/14* (2013.01); *G06T 2207/10136* (2013.01); *G06T 2207/30044* (2013.01); *G06T 2207/30048* (2013.01)

(56) References Cited

U.S. PATENT DOCUMENTS

| | | |
|---|---|---|
| 2004/0208341 A1 | 10/2004 | Zhou et al. |
| 2005/0074154 A1 | 4/2005 | Georgescu et al. |
| 2006/0116731 A1 | 6/2006 | Kramer et al. |
| 2006/0188135 A1 | 8/2006 | Zarkh et al. |
| 2007/0016005 A1 | 1/2007 | Timinger et al. |
| 2007/0049824 A1* | 3/2007 | Konofagou ............ A61B 8/08 600/437 |
| 2009/0005695 A1* | 1/2009 | Kosuda ................. A61B 5/02 600/500 |
| 2010/0198073 A1* | 8/2010 | Nishihara ............ A61B 8/483 600/443 |
| 2011/0190631 A1 | 8/2011 | Kramer et al. |
| 2011/0213249 A1 | 9/2011 | Nakata et al. |
| 2012/0123267 A1 | 5/2012 | Dow et al. |

FOREIGN PATENT DOCUMENTS

| | | |
|---|---|---|
| JP | 2005-533577 A | 11/2005 |
| JP | 2007-502186 A | 2/2007 |
| JP | 2007-509642 A | 4/2007 |
| JP | 2010-233966 A | 10/2010 |
| JP | 2011-177338 A | 9/2011 |
| JP | 2011-244931 A | 12/2011 |
| JP | 2012-531933 A | 12/2012 |
| WO | 2011/001309 A1 | 1/2011 |

OTHER PUBLICATIONS

Notification of Transmittal of Translation of the International Preliminary Report on Patentability (form PCT/IB/338) of International Application No. PCT/JP2013/054965, mailing date of Oct. 9, 2014, with form PCT/IPEA/409 (5 pages).

Office Action dated Sep. 2, 2015, issued in counterpart Chinese Application No. 201380016652.8, with English translation. (13 pages).

International Search Report dated Apr. 2, 2013, issued in corresponding application No. PCT/JP2013/054965.

Notice of Grounds for Rejection dated Mar. 26, 2013, issued in corresponding application No. PCT/JP2012/069055.

\* cited by examiner

DIAGNOSTIC ULTRASOUND APPARATUS

TECHNICAL FIELD

The present invention relates to an ultrasound diagnostic apparatus which diagnoses a fetus.

BACKGROUND ART

Ultrasound diagnostic apparatuses are being used in diagnosis of a tissue or the like in a living body, and are particularly important in diagnosis of a fetus. Under such a circumstance, various techniques related to diagnosis of the fetus by the ultrasound diagnostic apparatus have been proposed. For example, Patent Document 1 discloses an epoch-making technique that can measure a time difference of motion at each site of a cardiac muscle, for a heart or the like of the fetus.

However, for example, for a fetus of an early stage such as a fetus up to 10 weeks of pregnancy, the fetus itself is still small, and the heart is also very small. Thus, diagnosis of the heart by the ultrasound diagnostic apparatus is very difficult. For example, in the M-mode measurement or Doppler measurement of the ultrasound diagnostic apparatus, it is difficult to set the cursor or the like on the heart which is very small, and, even if the cursor or the like can be set, the overall fetus may move due to respiration of the mother or the like, causing the cursor or the like to be deviated from the heart, and making it difficult to maintain the precision of the measurement related to pulse information or the like.

Because of this, an improved technique is desired for the ultrasound diagnostic apparatus which can obtain, for example, pulse information for the fetus of early stage.

RELATED ART REFERENCE

Patent Document

[Patent Document 1] JP 2011-177338 A

DISCLOSURE OF INVENTION

Technical Problem

The present invention was made in view of the above-described background, and an advantage thereof is provision of an improved technique for an ultrasound diagnostic apparatus for obtaining pulse information of a fetus.

Solution to Problem

According to one aspect of the present invention, there is provided an ultrasound diagnostic apparatus comprising: a probe that transmits and receives ultrasound to and from a diagnosis region including a fetus; a transmitting and receiving unit that obtains a reception signal of the ultrasound from the diagnosis region by controlling the probe; a reference region setting unit that sets, in image data related to the diagnosis region obtained based on the reception signal, a body reference region for a body of the fetus and sets a cardiac reference region for a heart of the fetus; a shift analysis unit that analyses a motion of the body of the fetus using the body reference region in the image data to obtain shift information of the body; a cardiac motion analysis unit that analyzes a motion of the heart of the fetus using the cardiac reference region in the image data to obtain motion information of the heart; and a pulse information processor that obtains pulse information of the fetus based on the motion information of the heart from which the shift information of the body is subtracted.

In the above-described configuration, a preferred specific example of the image data related to the diagnosis region is, for example, data of a two-dimensional B-mode image (tomographic image), but data of a color Doppler image or a three-dimensional image may alternatively be used. In addition, the shape of the reference region (the body reference region and the cardiac reference region) may take various forms. For example, for two-dimensional image data, a reference region of a two-dimensional shape (rectangular, other polygons, circular, elliptical, or the like) may be used, and, for three-dimensional image data, a reference region of a three-dimensional shape may be used. The size of the reference region is set to a size corresponding to the body or the heart of the fetus, for example, and the body reference region is preferably larger than the cardiac reference region. In addition, for analysis of the motion of the body of the fetus and the motion of the heart of the fetus, tracking with the reference region as a template, a calculation of similarity targeted to the image data in the reference region, or the like, is employed.

According to the above-described configuration, there is provided an improved technique for an ultrasound diagnosis apparatus for obtaining the pulse information of the fetus. For example, because the pulse information of the fetus is obtained based on the motion information of the heart from which the shift information of the body is subtracted, the pulse information of the fetus can be obtained while reducing, or more preferably, completely removing, the influence of the shift due to the respiration of the mother or the motion or the like of the fetus itself. With this configuration, the pulse information of the fetus of an early stage up to about 10 weeks of pregnancy, for example, can be obtained with relatively high precision.

According to another aspect of the present invention, preferably, the shift analysis unit tracks the body reference region in the image data over a plurality of time phases, to form, as the shift information, a shift signal showing the motion of the body of the fetus over the plurality of time phases; the motion analysis unit tracks the cardiac reference region in the image data over a plurality of time phases, to form, as the motion information, a motion signal showing the motion of the heart of the fetus over the plurality of time phases; and the pulse information processor obtains the pulse information of the fetus based on a difference between the motion signal and the shift signal.

According to another aspect of the present invention, preferably, the shift analysis unit tracks the body reference region in the image data over a plurality of time phases, to obtain shift information which captures a motion of the body of the fetus over the plurality of time phases; the motion analysis unit moves the cardiac reference region in the image data over the plurality of time phases to follow the motion of the body of the fetus based on the shift information, and forms, as the motion information, a similarity signal showing a similarity of the image which changes over the plurality of time phases based on the image data in the cardiac reference region which is moved; and the pulse information processor obtains the pulse information of the fetus based on the similarity signal.

According to another aspect of the present invention, preferably, the reference region setting unit sets a relatively large body reference region including a boundary between the fetus and amniotic fluid, and sets a relatively small cardiac reference region including the heart of the fetus.

Advantageous Effects of Invention

According to various aspects of the present invention, an improved technique is provided for the ultrasound diagnostic apparatus for obtaining the pulse information of the fetus. For example, according to a preferred configuration of the present invention, the pulse information of the fetus can be obtained while reducing, or more preferably, completely removing, the influence of the shift due to the respiration of the mother or the motion or the like of the fetus itself. With this configuration, the pulse information of the fetus of an early stage up to, for example, about 10 weeks of pregnancy can be obtained with relatively high precision.

BEST MODE FOR CARRYING OUT THE INVENTION

Figure 1:
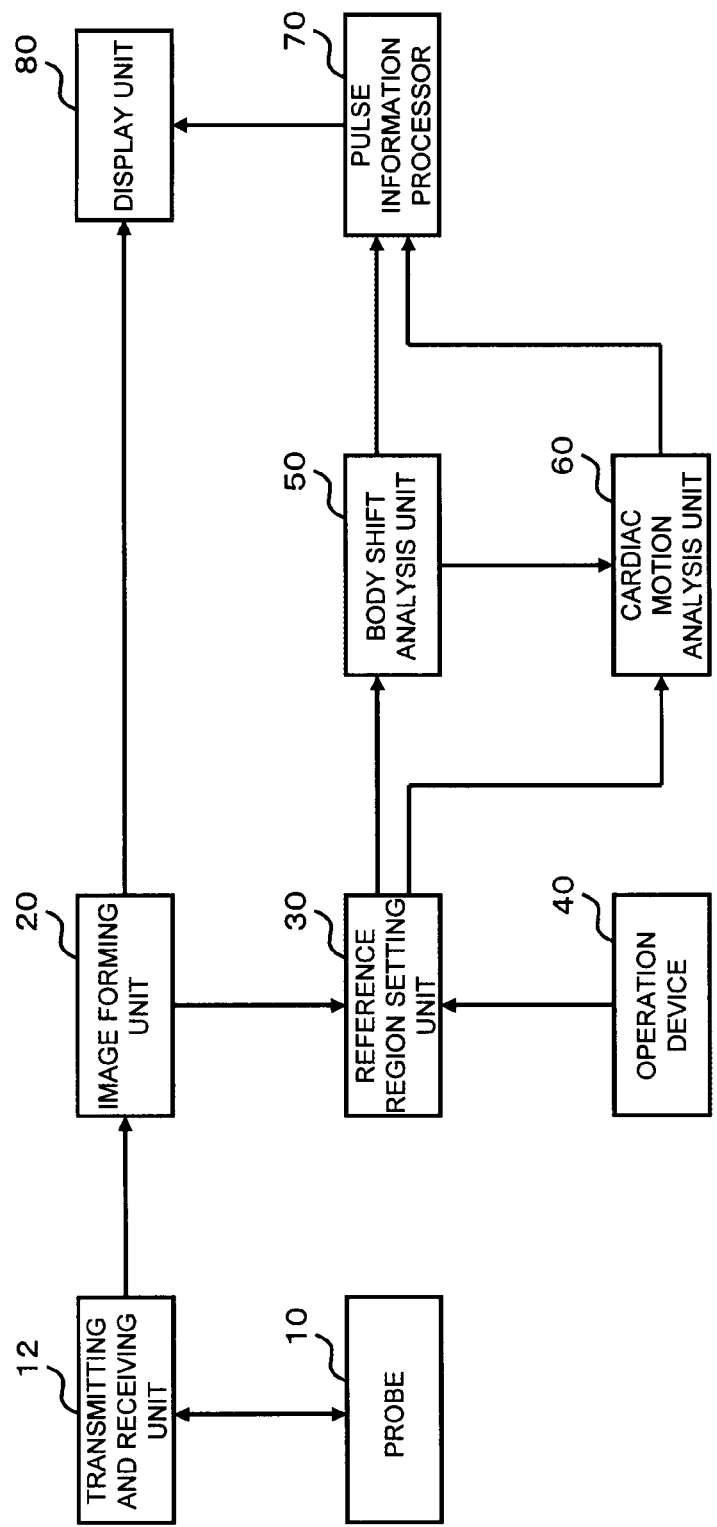
FIG. 1 is an overall structural diagram of an ultrasound diagnostic apparatus preferable in the present invention.

FIG. 1 is an overall structural diagram of an ultrasound diagnostic apparatus preferable in practicing the present invention ("present ultrasound diagnostic apparatus"). A probe 10 transmits ultrasound to a diagnosis region including a fetus and receives ultrasound reflected from the diagnosis region. The probe 10 has a plurality of transducer elements which transmit and receive ultrasound, and the plurality of the transducer elements are transmission-controlled by a transmitting and receiving unit 12, to form a transmission beam. In addition, the plurality of transducer elements receive the ultrasound reflected from the diagnosis region, a signal thus obtained is output to the transmitting and receiving unit 12, and the transmitting and receiving unit 12 forms a reception beam.

The transmitting and receiving unit 12 outputs a transmission signal corresponding to each of the plurality of transducer elements provided in the probe 10, to form a transmission beam of the ultrasound, and scans the transmission beam. In addition, the transmitting and receiving unit 12 applies a phasing and adding process or the like to a reception signal obtained from each of the plurality of transducer elements of the probe 10, to form a reception beam corresponding to the transmission beam which is scanned, and outputs echo data (reception signal) obtained along the reception beam.

An image forming unit 20 forms image data of an ultrasound image over a plurality of time phases related to the diagnosis region including the fetus based on the echo data (reception signal) obtained over the plurality of time phases. The image forming unit 20 forms, for example, image data of a tomographic image (B-mode image) showing the fetus for each frame (for each time phase) and over a plurality of time phases. The image data of the tomographic image formed in the image forming unit 20 are output to a reference region setting unit 30 sequentially for each frame. The image data formed in the image forming unit 20 are also output to a display unit 80 such as a monitor, and a tomographic image corresponding to the image data is displayed on the display unit 80.

The reference region setting unit 30 sets reference regions in the image data of the tomographic image formed by the image forming unit 20. The reference region setting unit 30 sets a body reference region for the body of the fetus and sets a cardiac reference region for the heart of the fetus. The reference region setting unit 30 sets the body reference region and the cardiac reference region, for example, according to a user operation which is input through an operation device 40. The user operates, for example, the operation device while viewing the tomographic image shown on the display unit 80 so that the body reference region and the cardiac reference region are set in desired positions. Alternatively, the reference region setting unit 30 may analyze the image state in the tomographic image, set the body reference region for the body of the fetus, and set the cardiac reference region of the heart of the fetus.

Figure 2:
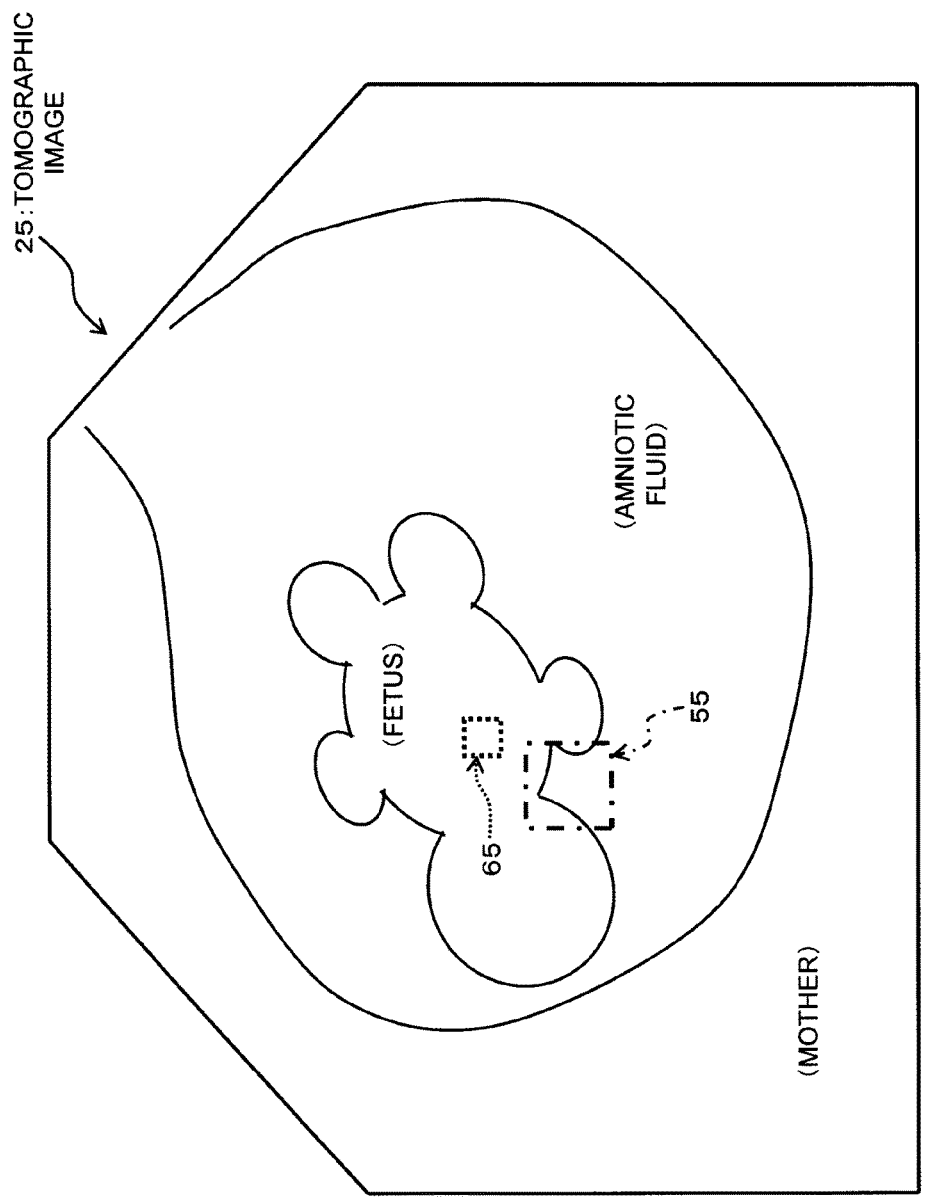
FIG. 2 is a diagram showing an example setting of a body reference region and a cardiac reference region.

FIG. 2 is a diagram showing an example setting of a body reference region 55 and a cardiac reference region 65. The tomographic image 25 shows the fetus in the mother (womb), and the fetus is surrounded by the amniotic fluid in the mother.

The body reference region 55 is used for analyzing the overall motion of the body of the fetus. For this purpose, the body reference region 55 is desirably set at a location where the motion of the body of the fetus can be easily detected. More specifically, for example, the user designates the position of the body reference region 55 to include a boundary between the fetus and the amniotic fluid. Alternatively, the present ultrasound diagnostic apparatus may determine the boundary between the fetus and the amniotic fluid through an image analysis process such as, for example, binarization, and designate the position of the body reference region 55. The body reference region 55 may alternatively be set at other locations where the motion of the body of the fetus can be easily detected.

The cardiac reference region 65 is used for analyzing a partial motion related to the heart of the fetus. For this purpose, the cardiac reference region 65 is preferably set at a location where the motion of the heart of the fetus can be easily detected. More specifically, for example, the user designates the position of the cardiac reference region 65 so that the heart portion of the fetus having a relatively high brightness is included. Alternatively, the present ultrasound diagnostic apparatus may determine the heart portion of the fetus having a relatively high brightness by an image analysis process such as, for example, binarization, and designate the position of the cardiac reference region 65. Alternatively, the cardiac reference region 65 may be set at other locations where the motion of the heart of the fetus can be easily detected.

In the specific example shown in FIG. 2, the body reference region 55 and the cardiac reference region 65 both have a rectangular shape, but the shapes of these reference regions may alternatively be other polygons, circles, ellipses, or the like. In addition, as shown in the specific example of FIG. 2, the cardiac reference region 65 is preferably relatively small to match the size of the heart of the fetus, and the body reference region 55 is preferably larger than the cardiac reference region 65 to match the size of the body of the fetus. The body reference region 55 and the cardiac reference region 65 may partially overlap each other. In addition, for example, a configuration may be employed in which only the position of the cardiac reference region 65 is designated, and the body reference region 55 is set to surround the cardiac reference region 65.

Referring again to FIG. 1, when the reference region setting unit 30 sets the body reference region and the cardiac reference region in the image data of the tomographic image, a body shift analysis unit 50 analyzes the motion of the body of the fetus using the body reference region in the image data of the tomographic image, to obtain shift information of the body. In addition, a cardiac motion analysis unit 60 analyzes the motion of the heart of the fetus using the cardiac reference region in the image data of the tomographic image, to obtain motion information of the heart. When the shift information of the body and the motion information of the heart are obtained in this manner, a pulse information processor 70 obtains pulse information of the fetus based on the motion information of the heart from which the shift information of the body is subtracted. The pulse information obtained by the pulse information processor 70 is displayed on the display unit 80.

The process from the setting of the reference regions to obtaining the pulse information will now be described in detail. For the structures (portions) already shown in FIGS. 1 and 2, the reference numerals thereof will be referred to also in the following description.

Figure 3:
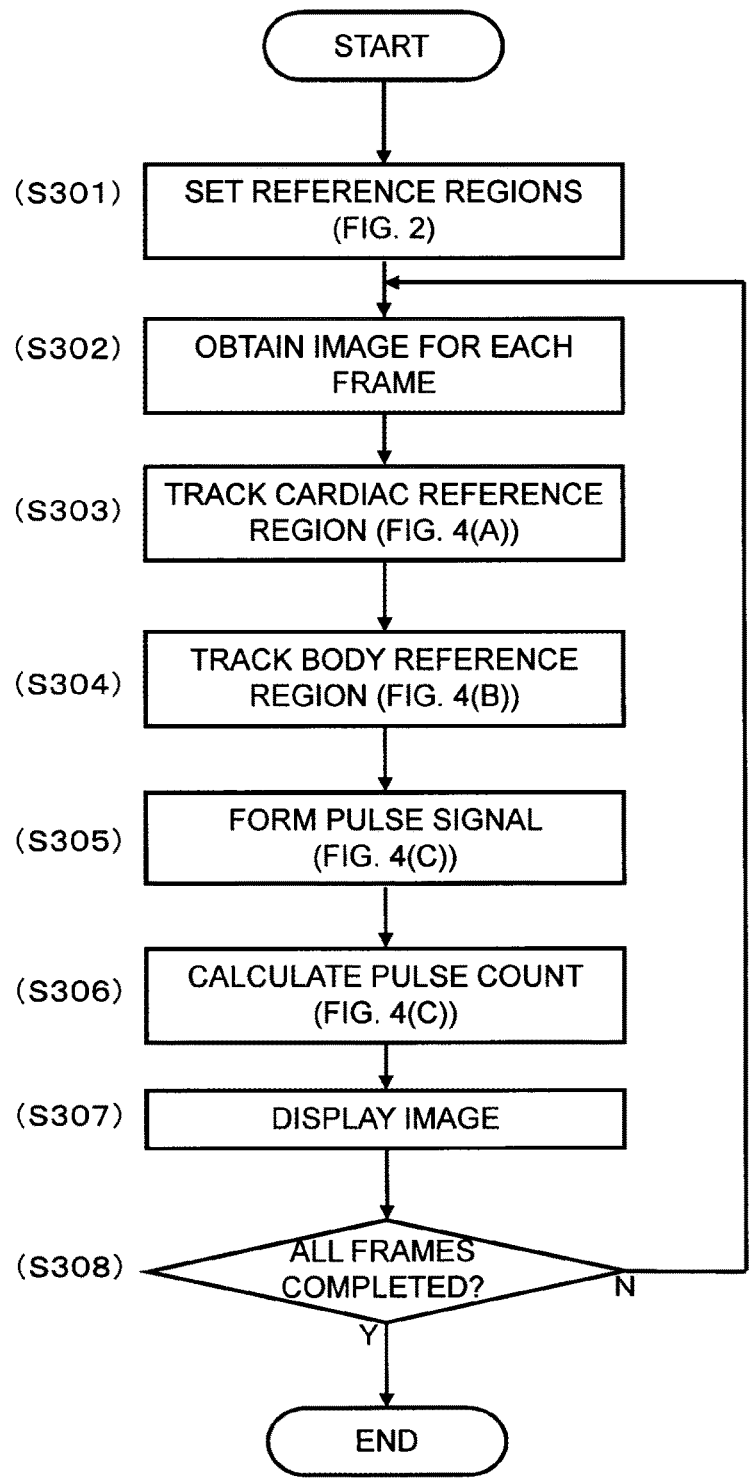
FIG. 3 is a diagram showing a specific example 1 of a process in the ultrasound diagnostic apparatus of FIG. 1.

FIG. 3 is a diagram showing a specific example 1 of a process in the ultrasound diagnostic apparatus of FIG. 1. First, when the ultrasound is transmitted and received, and the image data of the tomographic image related to the diagnosis region including the fetus are obtained, the reference region setting unit 30 sets the reference regions in the image data of the tomographic image (S301). For example, the body reference region 55 and the cardiac reference region 65 are set in the tomographic image of a frame which forms a standard (refer to FIG. 2).

Then, the body shift analysis unit 50 and the cardiac motion analysis unit 60 obtain image data of a tomographic image of a frame to be processed through the reference region setting unit 30 (S302). For example, the image data of the tomographic images of frames after the tomographic image for which the reference regions are set (standard frame) are sent to the body shift analysis unit 50 and the cardiac motion analysis unit 60 sequentially for each frame.

The cardiac motion analysis unit 60 tracks the cardiac reference region 65 in the image data of the tomographic image over a plurality of frames which are sequentially sent, to form a motion signal showing a motion of the heart of the fetus over the plurality of frames (S303). The body shift analysis unit 50 tracks the body reference region 55 in the image data of the tomographic image over a plurality of frames which are sequentially sent, to form a shift signal showing a motion of the body of the fetus over the plurality of frames (S304). The pulse information processor 70 forms a pulse signal of the fetus based on a difference between the motion signal and the shift signal (S305), and calculates a pulse count of the fetus based on the pulse signal (S306).

Figure 4:
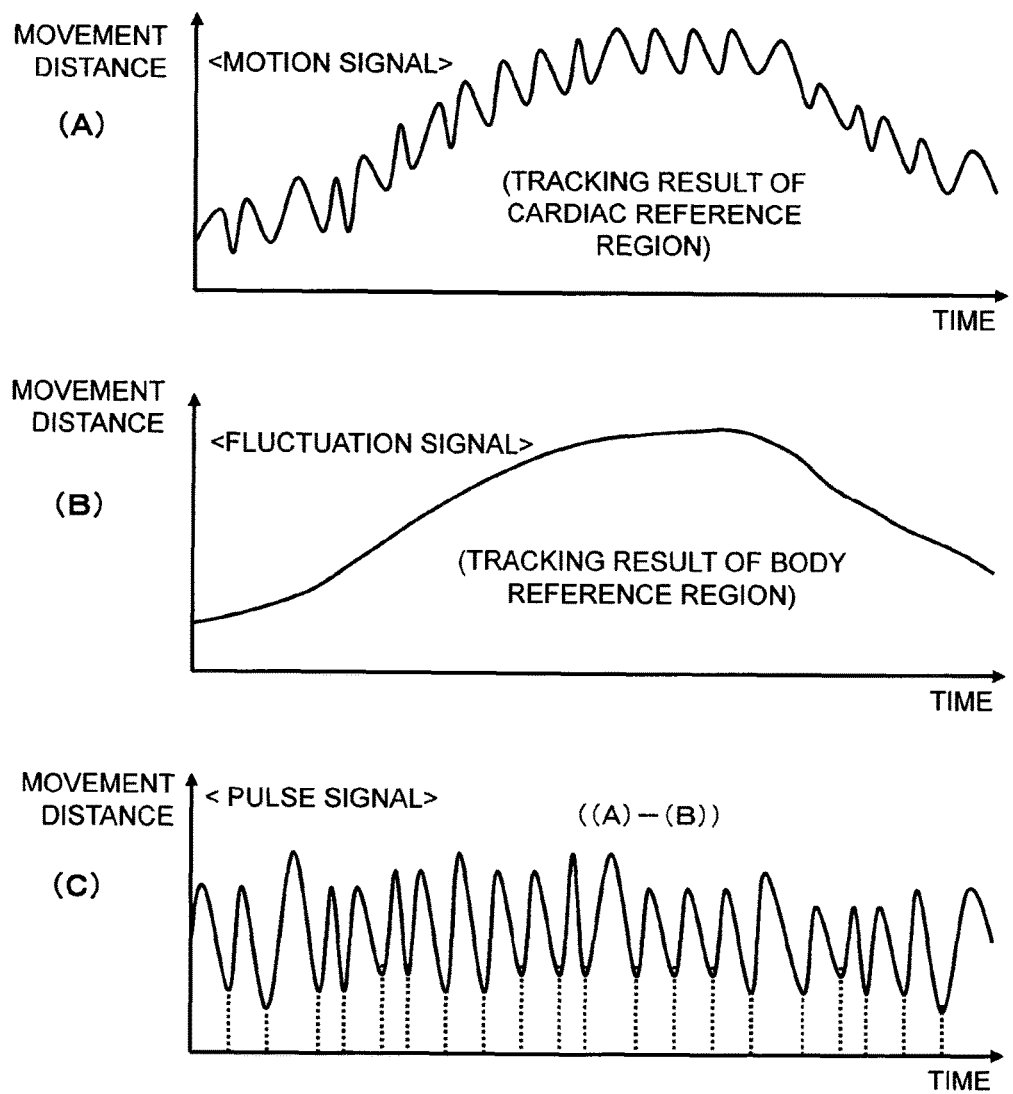
FIG. 4 is a diagram showing a signal obtained in the specific example 1.

FIG. 4 is a diagram showing a signal obtained in the specific example 1. FIG. 4(A) shows a waveform of a motion signal formed by the cardiac motion analysis unit 60. The horizontal axis represents time; that is, frame numbers of the frames which are sequentially processed, and the vertical axis represents a movement distance of the cardiac reference region 65. The cardiac motion analysis unit 60 executes a matching process to set, as a template, the cardiac reference region 65 (FIG. 2) which is set in the tomographic image of the standard frame, to search an image portion, in the tomographic image of the frame to be processed, which is most similar (having high correlation) to the image in the template, and to set the searched portion as the movement position of the template. In the tomographic image of the plurality of frames to be processed, the cardiac motion analysis unit 60 sequentially searches and tracks the movement position of the template.

The cardiac motion analysis unit 60 tracks the cardiac reference region 65 (template) over a plurality of frames, and calculates the movement distance of the cardiac reference region 65 for each frame. In other words, the cardiac motion analysis unit 60 calculates, for each frame, a distance from the position of the cardiac reference region 65 in the tomographic image of the standard frame to the movement position of the cardiac reference region 65 in the frame to be processed.

For example, when a plurality of pixels forming the tomographic image are arranged by an xy orthogonal coordinate system and tracking is executed in the xy orthogonal coordinate system, for each frame, the movement distance $d=\sqrt{(dx^2+dy^2)}$ is calculated based on an amount of movement dx in the x-axis direction and an amount of movement dy in the y-axis direction. In this manner, a waveform of a motion signal shown in FIG. 4(A) is obtained.

FIG. 4(B) shows a waveform of a shift signal formed by the body shift analysis unit 50. The horizontal axis represents time; that is, the frame numbers of the frames which are sequentially processed, and the vertical axis represents the movement distance of the body reference region 55. The body shift analysis unit 50 sets, as a template, the body reference region 55 (FIG. 2) which is set in the tomographic image of the standard frame, and sequentially executes tracking for searching the movement position of the template in the tomographic image of a plurality of frames to be processed. Similar to the formation process of the motion signal of FIG. 4(A), the body shift analysis unit 50 calculates, for each frame, a distance from the position of the body reference region 55 in the tomographic image of the standard frame to the movement position of the body reference region 55 in the frame to be processed, and forms the shift signal shown in FIG. 4(B).

FIG. 4(C) shows a waveform of a pulse signal formed by the pulse information processor 70. The pulse information processor 70 forms the pulse signal of FIG. 4(C) based on a difference between the motion signal of FIG. 4(A) and the shift signal of FIG. 4(B). More specifically, for each frame, the pulse processor 70 calculates a movement distance obtained by subtracting the movement distance of the shift signal from the movement distance of the motion signal, and forms the pulse signal shown in FIG. 4(C). In FIG. 4(C), the waveform of the pulse signal is enlarged in the direction of the vertical axis and is translated.

Because the pulse signal shown in FIG. 4(C) is a signal in which the shift information of the body is subtracted from the motion signal of the heart, the shift with respect to the body of the fetus is reduced, or more preferably, completely removed. Therefore, the pulse information processor 70 calculates the pulse count of the fetus, for example, based on the pulse signal. More specifically, for example, minimum values of the pulse signal are sequentially searched along the time axis direction which is the horizontal axis, and a time interval between adjacent minimum values is set as the time of one pulse. Because the time of one pulse may fluctuate in the time axis direction, for example, an average of times of one pulse obtained over a desired period is calculated. The pulse information processor 70 calculates the pulse count per unit time (heart rate) or the like, for example, based on the average of the time of one pulse.

In the calculation of the movement distances related to the signals of FIG. 4, each of movement distances in the x-axis direction and the y-axis direction may be used. For example, as the movement signal of FIG. 4(A), a waveform showing the movement distance in the x-axis direction over a plurality of frames and a waveform showing the movement distance in the y-axis direction over the plurality of frames may be formed. Similarly, for the shift signal of FIG. 4(B), the waveforms for the x-axis direction and for the y-axis direction may be formed, and, as the pulse signal of FIG. 4(C), a pulse signal related to the x-axis direction and a pulse signal related to the y-axis direction may be obtained. The pulse count may be calculated from each of the two pulse signals related to the x-axis direction and the y-axis direction. Alternatively, a combined movement distance $d=\sqrt{(x^2+y^2)}$ may be calculated based on the movement distance x of the pulse signal related to the x-axis direction and the movement distance y of the pulse signal related to the y-axis direction, and a waveform corresponding to FIG. 4(C) may be formed based on a change with respect to time of the combined movement distance d, to calculate the pulse count. Moreover, the coordinate system is not limited to the xy orthogonal coordinate system, and, for example, the signals of FIG. 4 may be obtained using an rθ scanning coordinate system.

Referring again to FIG. 3, when the pulse count of the fetus is calculated by the pulse information processor 70 (S306), the value of the pulse count and the tomographic image of the fetus are displayed on the display unit 80 (S307). It is then determined whether or not the processes related to all frames to be processed are completed (S308), the processes from S302 to S307 are repeated until the processes for all frames are completed, and, when the processes for all frames are completed, the present flowchart is also completed.

Figure 5:
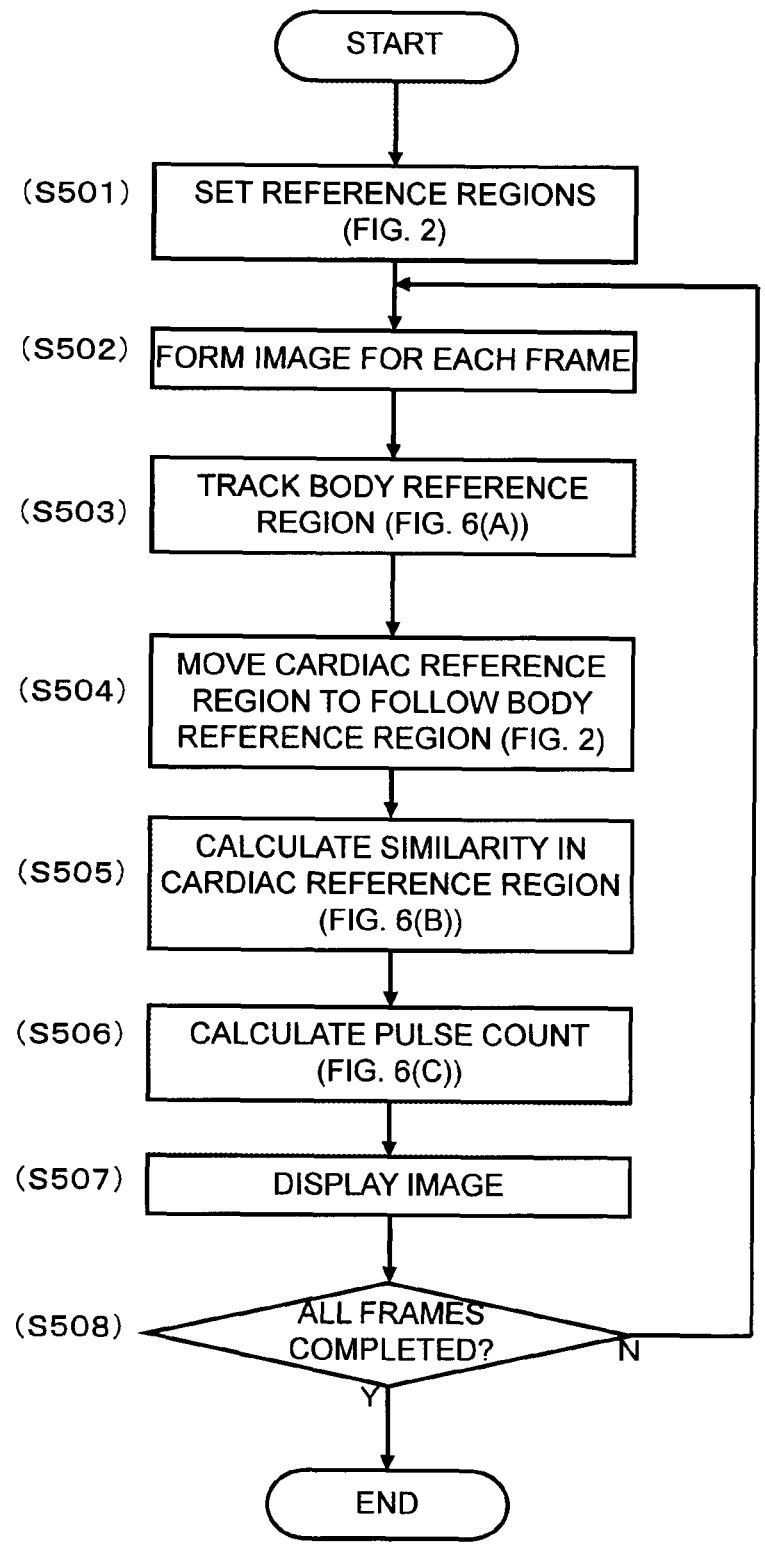
FIG. 5 is a diagram showing a specific example 2 of a process in the ultrasound diagnostic apparatus of FIG. 1.

FIG. 5 is a diagram showing a specific example 2 of the process in the ultrasound diagnostic apparatus of FIG. 1. First, when the ultrasound is transmitted and received and the image data of the tomographic image related to the diagnosis region including the fetus are obtained, the reference region setting unit 30 sets the reference regions in the image data of the tomographic image (S501). For example, in the tomographic image of a frame which forms a standard, the body reference region 55 and the cardiac reference region 65 are set (refer to FIG. 2).

Then, the body shift analysis unit 50 and the cardiac motion analysis unit 60 obtain the image data of the tomographic image of a frame to be processed through the reference region setting unit 30 (S502). For example, image data of the tomographic images of the frames after the tomographic image in which the reference regions are set (frame which forms the standard) are sequentially sent to the body shift analysis unit 50 and the cardiac motion analysis unit 60 for each frame.

The body shift analysis unit 50 tracks the body reference region 55 in the image data of the tomographic image over a plurality of frames which are sequentially sent, to obtain the shift information capturing the motion of the body of the fetus over the plurality of frames (S503). Based on the shift information, the cardiac motion analysis unit 60 moves the cardiac reference region 65 in the image data of the tomographic image over the plurality of frames which are sequentially sent, to follow the motion of the body of the fetus (S504). Further, the cardiac motion analysis unit 60 calculates similarity of the image which changes over the plurality of frames based on the image data in the cardiac reference region 654 which is moved, to form a similarity signal (S505). The pulse information processor 70 calculates the pulse count of the fetus based on the similarity signal (S506).

Figure 6:
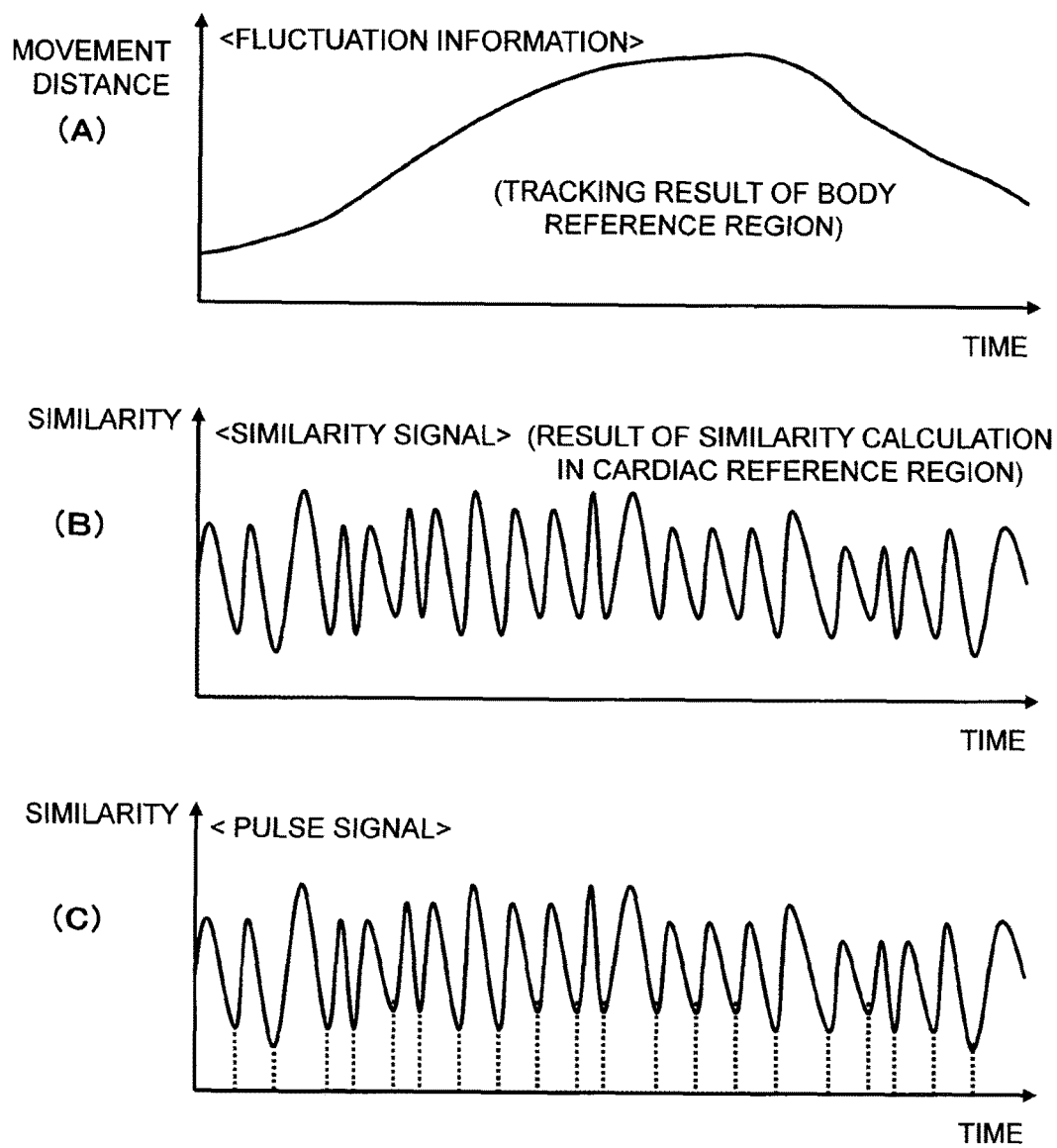
FIG. 6 is a diagram showing a signal obtained in the specific example 2.

FIG. 6 is a diagram showing a signal obtained in the specific example 2. FIG. 6(A) shows the shift information formed by the body shift analysis unit 50. The horizontal axis represents time; that is, the frame numbers of the frames which are sequentially processed, and the vertical axis represents the movement distance of the body reference region 55. The body shift analysis unit 50 executes a matching process to set, as a template, the body reference region 55 which is set in the tomographic image of the standard frame (FIG. 2), to search, in the tomographic image of the frame to be processed, an image portion which is most similar (having high correlation) to the image in the template, and to set the searched portion as the movement position of the template. The body shift analysis unit 50 sequentially searches and tracks the movement position of the template in the tomographic images of the plurality of frames to be processed.

The body shift analysis unit 50 tracks the body reference region 55 (template) over a plurality of frames, and calculates the movement distance of the body reference region 55 for each frame. In other words, the body shift analysis unit 50 calculates for each frame a distance from the position of the body reference region 55 in the tomographic image of the standard frame to the movement position of the body reference region 55 in the frame to be processed.

For example, when a plurality of pixels forming the tomographic image are arranged in an xy orthogonal coordinate system and the tracking is executed in the xy orthogonal coordinate system, a movement distance dx in the x-axis direction and a movement distance dy in the y-axis direction are obtained for each frame. In this manner, a waveform of the shift information shown in FIG. 6(A) is obtained for each of the x-axis direction and the y-axis direction.

The cardiac motion analysis unit 60 moves the cardiac reference region 65 by the same distance as the movement distance of the body reference region 55 in the image data of the tomographic image over the plurality of frames which are sequentially sent. In other words, the cardiac motion analysis unit 60 moves, for each frame, the cardiac reference region 65 in the x-axis direction by the same distance as the movement distance dx in the x-axis direction of the body reference region 55, and moves the cardiac reference region 65 in the y-axis direction by the same distance as the movement distance dy in the y-axis direction of the body reference region 55. With this process, the cardiac motion analysis unit 60 moves the cardiac reference region 65 to follow the movement of the body reference region 55; that is, the motion of the body of the fetus.

In the tracking of the body reference region 55 and the movement of the cardiac reference region 65, the coordinate system is not limited to the xy orthogonal coordinate system, and alternatively, for example, the re scanning coordinate system may be employed.

The cardiac motion analysis unit 60 calculates similarity of the image which changes over the plurality of frames based on the image data in the cardiac reference region 65 which is moved, to form a similarity signal. In other words, the cardiac motion analysis unit 60 calculates for each frame a similarity (for example, correlation) between the image data in the cardiac reference region 65 in the tomographic image of the standard frame and the image data in the cardiac reference region 65 in the frame to be processed. In this manner, the waveform of the similarity signal shown in FIG. 6(B) is obtained.

In obtaining the similarity signal of FIG. 6(B), because the cardiac reference region 65 is moved to follow the motion of the body of the fetus, the influence of the shift related to the body of the fetus is reduced or more preferably completely removed in the similarity signal. Thus, the pulse information processor 70 assumes the similarity signal as a pulse signal, and calculates, for example, the pulse count of the fetus based on the pulse signal.

More specifically, for example, as shown in FIG. 6(C), minimum values of the pulse signal are sequentially searched along the time axis direction which is the horizontal direction, and a time interval between adjacent minimum values is set as a time of one pulse. However, because the time of one pulse may fluctuate in the time axis direction, for example, an average of the time of one pulse obtained over a desired period is calculated. The pulse information processor 70 calculates, for example, a pulse count per unit time (heart rate) or the like based on the average of the time of one pulse.

Referring again to FIG. 5, when the pulse count of the fetus is calculated by the pulse information processor 70 (S506), the value of the pulse count and the tomographic image of the fetus are displayed on the display unit 80 (S507). It is then determined whether or not processes for all frames to be processed are completed (S508), processes from S502 to S507 are repeated until the processes for all frames are completed, and, when the processes for all frames are completed, the present flowchart is also completed.

A preferred embodiment of the present invention has been described. However, the above-described embodiment is merely exemplary in every aspect, and is not intended to limit the scope of the present invention. The present invention includes various modified forms within the scope and spirit of the present invention.

EXPLANATION OF REFERENCE NUMERALS

10 PROBE; 12 TRANSMITTING AND RECEIVING UNIT; 20 IMAGE FORMING UNIT; 30 REFERENCE REGION SETTING UNIT; 50 BODY SHIFT ANALYSIS UNIT; 60 CARDIAC MOTION ANALYSIS UNIT; 70 PULSE INFORMATION PROCESSOR; 80 DISPLAY UNIT.

The invention claimed is:

1. An ultrasound diagnostic apparatus comprising:
a probe that transmits and receives ultrasound to and from a diagnosis region including a fetus;
a transmitting and receiving unit that obtains a reception signal of the ultrasound from the diagnosis region by controlling the probe;
a reference region setting unit that sets, in image data related to the diagnosis region obtained based on the reception signal, a body reference region for a body of the fetus and sets a cardiac reference region for a heart of the fetus;
a shift analysis unit that analyzes a motion of the body of the fetus using the body reference region in the image data to obtain shift information of the body;
a motion analysis unit that analyzes a motion of the heart of the fetus using the cardiac reference region in the image data to obtain motion information of the heart; and
a pulse information processor that obtains pulse information of the fetus based on the motion information of the heart from which the shift information of the body is subtracted.

2. The ultrasound diagnostic apparatus according to claim 1, wherein
the shift analysis unit tracks the body reference region in the image data over a plurality of time phases, to form, as the shift information, a shift signal showing the motion of the body of the fetus over the plurality of time phases,
the motion analysis unit tracks the cardiac reference region in the image data over a plurality of time phases, to form, as the motion information, a motion signal showing the motion of the heart of the fetus over the plurality of time phases, and
the pulse information processor obtains the pulse information of the fetus based on a difference between the motion signal and the shift signal.

3. The ultrasound diagnostic apparatus according to claim 2, wherein
the shift analysis unit calculates a movement distance from a position of the body reference region in image data of a time phase which becomes a standard to a movement position of the body reference region in each time phase to be processed, and forms the shift signal showing the movement distance of the body reference region over the plurality of time phases.

4. The ultrasound diagnostic apparatus according to claim 2, wherein
the motion analysis unit calculates a movement distance from a position of the cardiac reference region in image data of a time phase which becomes a standard to a movement position of the cardiac reference region in each time phase to be processed, and forms the motion signal showing the movement distance of the cardiac reference region over the plurality of time phases.

5. The ultrasound diagnostic apparatus according to claim 2, wherein
the shift analysis unit calculates a movement distance from a position of the body reference region in image data of a time phase which becomes a standard to a movement position of the body reference region in each time phase to be processed,
the motion analysis unit calculates a movement distance from a position of the cardiac reference region in the image data of the time phase which becomes the standard to a movement position of the cardiac reference region in each time phase to be processed, and
the pulse information processor calculates, for each time phase, a difference movement distance obtained by subtracting the movement distance of the body reference region from the movement distance of the cardiac reference region, and forms a pulse signal showing the difference movement distance over the plurality of time phases.

6. The ultrasound diagnostic apparatus according to claim 1, wherein
the shift analysis unit tracks the body reference region in the image data over a plurality of time phases, to obtain shift information which captures a motion of the body of the fetus over the plurality of time phases,
the motion analysis unit moves the cardiac reference region in the image data over the plurality of time phases to follow the motion of the body of the fetus based on the shift information, and forms, as the motion information, a similarity signal formed by calculating for each frame in the image data a correlation between the image data in the cardiac reference region in a tomographic image of a standard frame and the image data in the cardiac reference region in a frame to be processed, and the pulse information processor obtains the pulse information of the fetus based on the similarity signal.

7. The ultrasound diagnostic apparatus according to claim 6, wherein the shift analysis unit calculates a movement distance from a position of the body reference region in image data of a time phase which becomes a standard to a movement position of the body reference region in each time phase to be processed.

8. The ultrasound diagnostic apparatus according to claim 6, wherein the shift analysis unit calculates a movement distance from a position of the body reference region in image data of a time phase which becomes a standard to a movement position of the body reference region in each time phase to be processed, and the motion analysis unit moves, in the image data, the cardiac reference region by the same distance as the movement distance of the body reference region for each time phase over a plurality of time phases, to move the cardiac reference region to follow the movement of the body reference region.

9. The ultrasound diagnostic apparatus according to claim 6, wherein the motion analysis unit calculates a similarity between image data in the cardiac reference region at a time phase which becomes a standard and image data in the cardiac reference region in each time phase to be processed, and forms a similarity signal showing the similarity over a plurality of time phases.

10. The ultrasound diagnostic apparatus according to claim 1, wherein the reference region setting unit sets a relatively large body reference region including a boundary between the fetus and amniotic fluid, and sets a relatively small cardiac reference region including the heart of the fetus.

11. The ultrasound diagnostic apparatus according to claim 1, wherein the reference region setting unit determines a boundary between the fetus and amniotic fluid in the image data, and sets the body reference region including the boundary.

12. The ultrasound diagnostic apparatus according to claim 1, wherein the reference region setting unit determines a cardiac portion of the fetus having a relatively high brightness in the image data by a binarization process, and sets the cardiac reference region to include the cardiac portion.

* * * * *